US009928451B2

(12) United States Patent
Dai

(10) Patent No.: US 9,928,451 B2
(45) Date of Patent: Mar. 27, 2018

(54) INFORMATION PROCESSING APPARATUS, CONTROLLING METHOD, AND COMPUTER-READABLE STORAGE MEDIUM

(71) Applicant: CANON KABUSHIKI KAISHA, Tokyo (JP)

(72) Inventor: Xiaoyan Dai, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 46 days.

(21) Appl. No.: 14/444,697

(22) Filed: Jul. 28, 2014

(65) Prior Publication Data

US 2015/0036929 A1 Feb. 5, 2015

(30) Foreign Application Priority Data

Jul. 31, 2013 (JP) .................................. 2013-159741

(51) Int. Cl.
*G06K 9/00* (2006.01)
*G06K 9/72* (2006.01)
*G06F 19/00* (2018.01)

(52) U.S. Cl.
CPC ........... *G06K 9/723* (2013.01); *G06F 19/322* (2013.01); *G06F 19/327* (2013.01); *G06F 19/363* (2013.01); *G06K 9/00449* (2013.01); *G06K 2209/01* (2013.01)

(58) Field of Classification Search
None
See application file for complete search history.

(56) References Cited

U.S. PATENT DOCUMENTS

| | | | | |
|---|---|---|---|---|
| 2006/0036472 | A1* | 2/2006 | Crockett | G06F 19/322 705/3 |
| 2006/0177135 | A1* | 8/2006 | Fujita | G06K 9/2054 382/187 |
| 2007/0174079 | A1* | 7/2007 | Kraus | G06Q 10/10 705/3 |
| 2008/0212901 | A1* | 9/2008 | Castiglia | G06K 9/033 382/311 |
| 2009/0138284 | A1* | 5/2009 | Guadagna | G06F 19/322 705/3 |
| 2009/0219567 | A1* | 9/2009 | Ishizaki | G06K 9/00449 358/1.15 |
| 2010/0054599 | A1* | 3/2010 | Itonori | G06K 9/03 382/177 |

(Continued)

FOREIGN PATENT DOCUMENTS

| JP | 2004-30257 A | 1/2004 |
|---|---|---|
| JP | 2004-252607 A | 9/2004 |

*Primary Examiner* — Ryan P Potts
(74) *Attorney, Agent, or Firm* — Canon U.S.A., Inc. IP Division

(57) ABSTRACT

An information processing apparatus includes an information recognition unit, an acquiring unit, and a recording unit. The information recognition unit recognizes a description written in each of one or more description areas. The acquiring unit acquires attribute information of the description area in which the description is written. The recording unit records the description written in the description area or a recognition result obtained through the recognition performed by the information recognition unit in accordance with the attribute information acquired by the acquiring unit.

10 Claims, 12 Drawing Sheets

(56) References Cited

U.S. PATENT DOCUMENTS

| | | | |
|---|---|---|---|
| 2010/0188419 A1* | 7/2010 | Ratnakar | G06K 9/033 345/619 |
| 2011/0096983 A1* | 4/2011 | Jensen | G06K 9/033 382/161 |
| 2011/0280481 A1* | 11/2011 | Radakovic | G06K 9/033 382/177 |
| 2013/0238358 A1* | 9/2013 | Yamane | G06F 19/324 705/3 |

* cited by examiner

FIG. 4

| AREA ID | AREA NAME | AREA BOUNDS (mm) | ATTRIBUTE CLASSIFICATION |
|---|---|---|---|
| 01 | S | 10, 10, 188, 60 | 1 |
| 02 | O | 10, 70, 188, 110 | 2 |
| 03 | A | 10, 120, 188, 160 | 2 |
| 04 | P | 10, 170, 188, 220 | 2 |

FIG. 6A

S 1. Precordial pain after exertion since about ten days ago.
     It occurs for a few hours, and has occurred several
     times in past two days.
            ⌒
            these Irradiating pain in the back.

2. "Feel chest pain after exertion.
      It has occurred since ten days ago."

O PHYSICAL FINDINGS     cm    kg
  BLOOD PRESSURE  110—72 Hg
  CARDIOPULMONARY AUSCULTATION
  AND PERCUSSION
  PALPATION OF ABDOMEN

A 1. Differential diagnosis of acute chest pain
  2. D.D. of repeated chest pain P ECG findings(tt)
  Recommend a division of cardiovascular disease.

FIG. 6B

S 1. Precordial pain after exertion since about ten days ago.
     It occurs for a few hours, and has occurred several
     times in past two days.
            ⌒
            these Irradiating pain in the back.

2. "Feel chest pain after exertion.
      It has occurred since ten days ago."

O PHYSICAL FINDINGS
  BLOOD PRESSURE
  CARDIOPULMONARY AUSCULTATION
  AND PERCUSSION
  PALPATION OF ABDOMEN

A 1. DIFFERENTIAL DIAGNOSIS OF
     ACUTE CHEST PAIN
  2. MEDICINE ******

P ECG FINDINGS
  RECOMMEND A DIVISION OF CARDIOVASCULAR
  DISEASE.

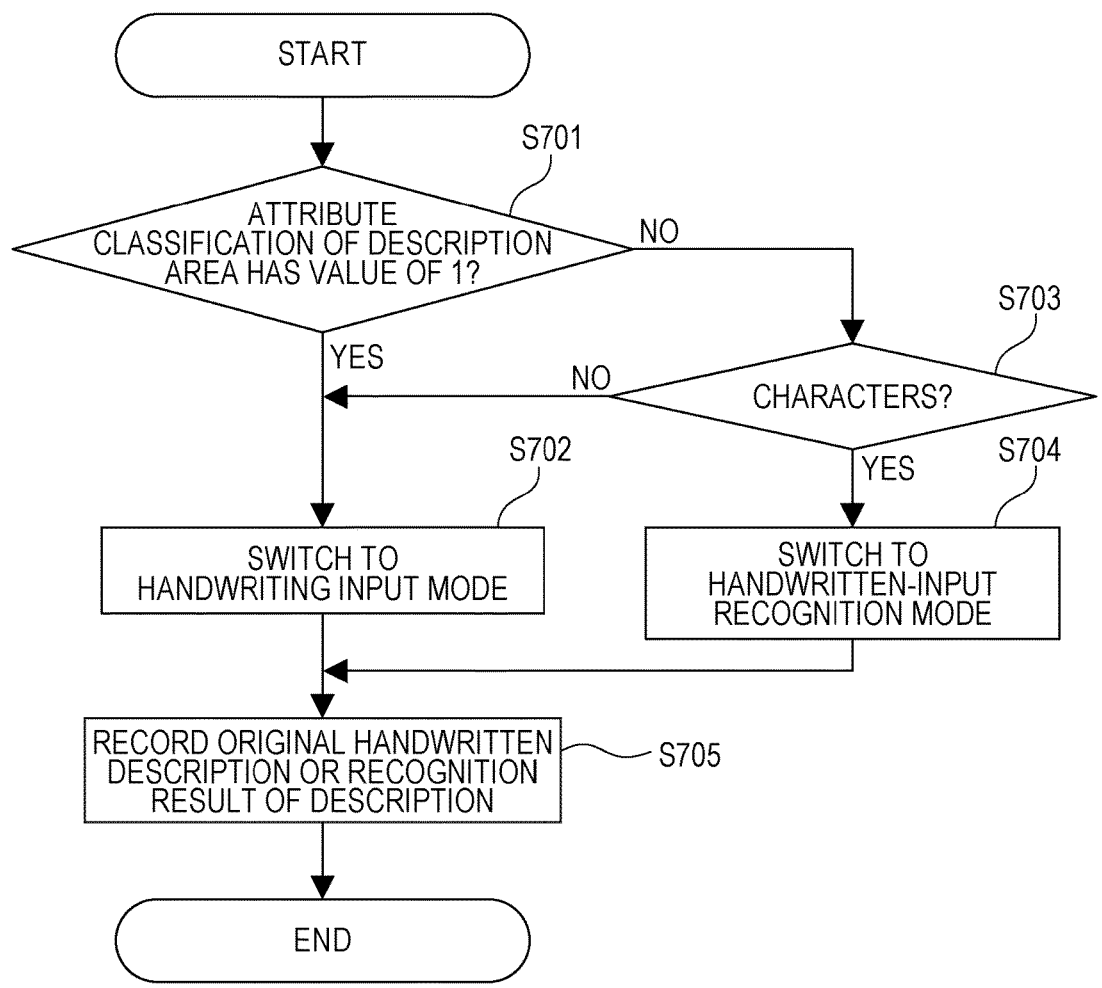

FIG. 8A

S  1. Precordial pain after exertion since about ten days ago. It occurs for a few hours, and has occurred several times in past two days.
      these
   Irradiating pain in the back.
   2. "Feel chest pain after exertion. It has occurred since ten days ago."

O  PHYSICAL FINDINGS    cm    kg
   BLOOD PRESSURE  110-72  Hg
   CARDIOPULMONARY AUSCULTATION AND PERCUSSION
   PALPATION OF ABDOMEN

A  1. Differential diagnosis of acute chest pain
   2. D.D. of repeated chest pain P  ECG findings (++)
   Recommend a division of cardiovascular disease.

FIG. 8B

S  1. Precordial pain after exertion since about ten days ago. It occurs for a few hours, and has occurred several times in past two days.
      these
   Irradiating pain in the back.
   2. "Feel chest pain after exertion. It has occurred since ten days ago."

O  PHYSICAL FINDINGS
   BLOOD PRESSURE
   CARDIOPULMONARY AUSCULTATION AND PERCUSSION
   PALPATION OF ABDOMEN

A  1. DIFFERENTIAL DIAGNOSIS OF ACUTE CHEST PAIN
   2. MEDICINE ******

P  ECG FINDINGS
   RECOMMEND A DIVISION OF CARDIOVASCULAR DISEASE.

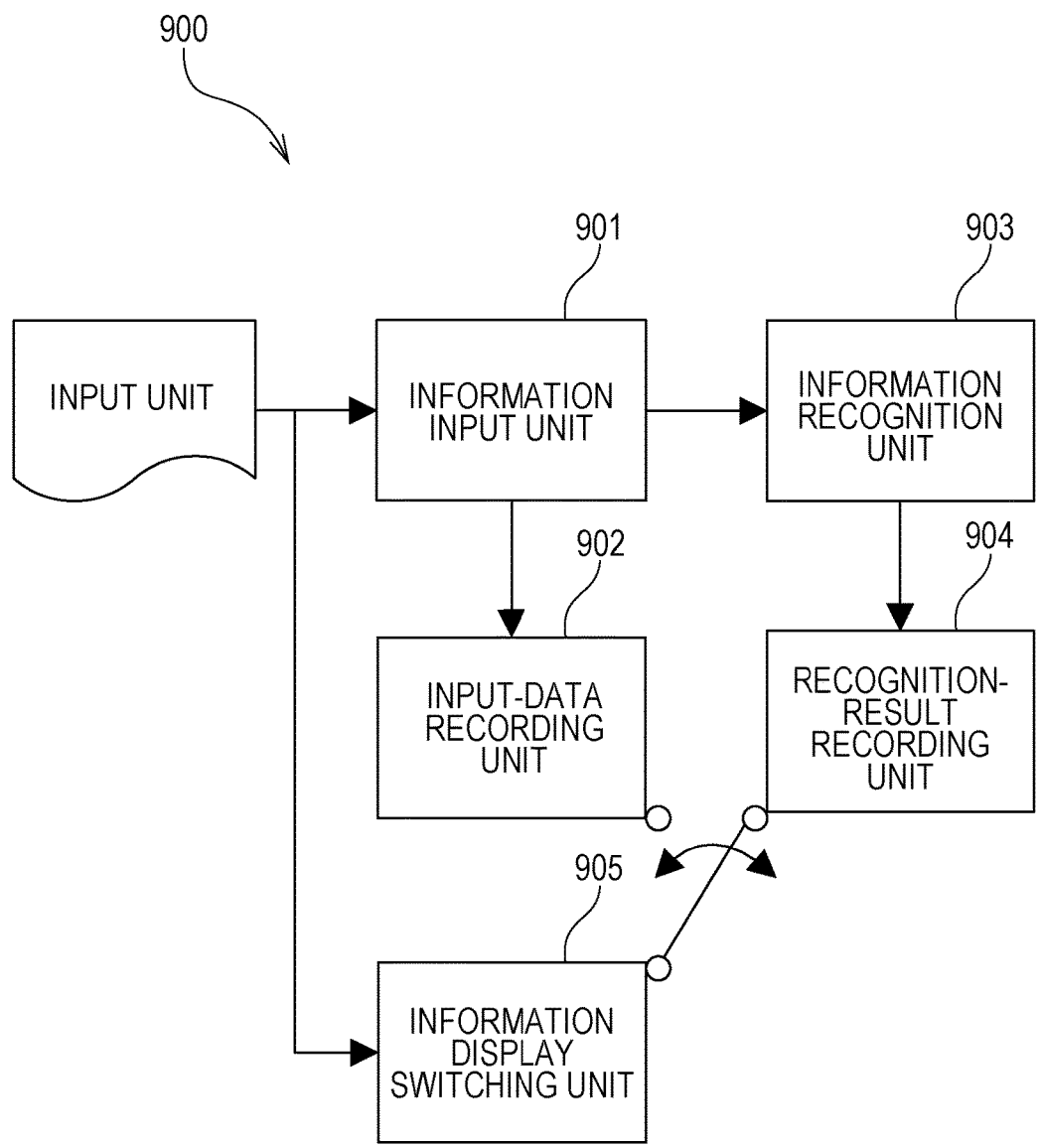

FIG. 10A

6/15/2003
S 1. Precordial pain after exertion since about ten days ago.
   It occurs for a few hours, and has occurred several
   times in past two days.
        these
   Irradiating pain in the back.
  2. "Feel chest pain after exertion."
     It has occurred since ten days ago.
O  PHYSICAL FINDINGS   cm   kg
   BLOOD PRESSURE  110 — 172 Hg
   CARDIOPULMONARY AUSCULTATION
   AND PERCUSSION
   PALPATION OF ABDOMEN
A  1. Differential diagnosis of acute chest pain
   2. D.D. of repeated chest pain
P  ECG findings(↑)
   Recommend a division of cardiovascular disease.

FIG. 10B

S  1. PRECORDIAL PAIN AFTER EXERTION *******
      ************************************
   2. "FEEL CHEST PAIN AFTER EXERTION. *******
      *********************************

O  PHYSICAL FINDINGS
   BLOOD PRESSURE
   CARDIOPULMONARY AUSCULTATION
   AND PERCUSSION
   PALPATION OF ABDOMEN

A  1. DIFFERENTIAL DIAGNOSIS OF
      ACUTE CHEST PAIN
   2. MEDICINE ******

P  ECG FINDINGS
   RECOMMEND A DIVISION OF CARDIOVASCULAR
   DISEASE.

FIG. 11B

6/15/2003 — CHARACTER AREA 1

S  1. PRECORDIAL PAIN AFTER EXERTION *******
      *********************************
   2. "FEEL CHEST PAIN AFTER EXERTION. *******
      ****************************

— CHARACTER AREA 2

O  PHYSICAL FINDINGS
   BLOOD PRESSURE
   CARDIOPULMONARY AUSCULTATION
   AND PERCUSSION
   PALPATION OF ABDOMEN

— CHARACTER AREA 3

A  1. DIFFERENTIAL DIAGNOSIS OF
      ACUTE CHEST PAIN
   2. MEDICINE ******

— CHARACTER AREA 4

P  ECG FINDINGS
   RECOMMEND A DIVISION OF CARDIOVASCULAR
   DISEASE.

FIG. 11A

6/15/2003
S  1. Precordial pain after exertion since about ten days ago.
      It occurs for a few hours, and has occurred several
      times in past two days.
         these
      Irradiating pain in the back.
   2. "Feel chest pain after exertion."
      It has occurred since ten days ago.

O  PHYSICAL FINDINGS        cm    kg
   BLOOD PRESSURE   110 — 72 Hg
   CARDIOPULMONARY AUSCULTATION     up
   AND PERCUSSION
   PALPATION OF ABDOMEN

A  1. Differential diagnosis of acute chest pain
   2. D.D. of repeated chest pain P  ECG findings(tt)
   Recommend a division of cardiovascular disease.

FIG. 11C

| ATTRIBUTE CLASSIFICATION | STRING TO BE CONTAINED | | |
|---|---|---|---|
| | O | FINDINGS | TEST |
| 1 | A | DETERMINE | MEDICINE |
| 1 | P | RECOMMEND | TREATMENT |
| 1 | ... | ... | ... |

FIG. 11D

6/15/2003
S 1. Precordial pain after exertion since about ten days ago. It occurs for a few hours, and has occurred several times in past two days.
   ~these
   Irradiating pain in the back.
 2. "Feel chest pain after exertion. It has occurred since ten days ago."

O  PHYSICAL FINDINGS
   BLOOD PRESSURE
   CARDIOPULMONARY AUSCULTATION
   AND PERCUSSION
   PALPATION OF ABDOMEN

A  1. DIFFERENTIAL DIAGNOSIS OF
      ACUTE CHEST PAIN
   2. MEDICINE ******

P  ECG FINDINGS
   RECOMMEND A DIVISION OF CARDIOVASCULAR DISEASE.

INFORMATION PROCESSING APPARATUS, CONTROLLING METHOD, AND COMPUTER-READABLE STORAGE MEDIUM

BACKGROUND

Field

Aspects of the present invention generally relate to an information processing apparatus, a controlling method, and a computer-readable storage medium.

Description of the Related Art

Heretofore, in the medical field such as hospitals, paper medical records having a predetermined format have been used to record the condition and the treatment process of a patient. A paper medical record is constituted by four description areas abbreviated to SOAP. The character S represents the main complaints of a patient. The character O represents information obtained through physical examinations/tests. The character A represents a disease evaluation made by a doctor. The character P represents a treatment plan made on the basis of the above-described data. Among these description areas, the S area is mainly referred to by a doctor. The other areas other than the S area, in which test information and a prescription for medicine are described, are referred to when a medical practice is performed by a nurse or when paperwork is performed by a staff in Medical Professions Division.

Advantages of paper medical records are, for example, that it is easy to use because a doctor can fill out a medical record while looking at and listening to a patient, and that the handwriting reminds a doctor of a deep nuance of the description and a scene of diagnosis. However, a handwritten description about medical-treatment information which is to be shared among sections is difficult to read, and time and effort are required to check the description. For paper medical records, it has been pointed out that a storage area is required, that manpower is required for transcription which is not a meaningful task, or that it is difficult to perform a search using paper medical records. Therefore, a shift from paper medical records to electronic medical records has progressed.

The shift from paper medical records to electronic medical records achieves unified management and sharing of medical-treatment information. This eliminates time and effort for a traditional operation of writing medical-treatment information by hand multiple times, resulting in a reduction in transcription errors. A large amount of data can be easily searched for necessary medical-treatment information, and the problem of storage space for paper medical records can be reduced.

However, use of an electronic medical record involves operations based on a complicated specification. In limited consultation hours, a doctor may fail to communicate with a patient because the doctor concentrates on input operations, and the doctor may miss hearing important information. In addition, all of the input data is shaped, making it difficult for the handwriting or the like to remind a doctor of a scene of diagnosis.

Therefore, to combine the advantages of paper medical records and those of electronic medical records, various proposals about data input and data management of electronic medical records have been made. In Japanese Patent Laid-Open No. 2004-252607, a technique is described. In the technique, a medical record in which minute points are previously printed over the entire surface of a sheet is filled out; medical care record data including a description and its position coordinates is generated; and the generated electronic data is managed over a network. The technique proposed in Japanese Patent Laid-Open No. 2004-252607 achieves high operability, enables input of medical record information which is the same as that written by hand, and enables medical care information to be recorded and used on a time-series basis even among sections or among medical institutions. In Japanese Patent Laid-Open No. 2004-30257, a technique is proposed. In the technique, patient information handwritten on a data sheet is obtained by using an electronic pen; the obtained information is transmitted to a server; the server performs authentication to check if the patient is a patient who is to be nursed, on the basis of the written patient information; and the authentication result is transmitted to a staff.

However, in these techniques of the related art, all of the descriptions on a paper medium are converted into electronic forms. Therefore, a description from which memories are desirably evoked and a description that desirably remains as handwriting information fail to be checked.

SUMMARY

Aspects of the present invention generally enable a user to check a description as it is or the recognition result of a description in accordance with the user's desire.

According to an aspect of the present invention, an information processing apparatus includes an information recognition unit configured to recognize a description written in each of one or more description areas, an acquiring unit configured to acquire attribute information of the description area in which the description is written, and a recording unit configured to record the description written in the description area or a recognition result obtained through the recognition performed by the information recognition unit in accordance with the attribute information acquired by the acquiring unit.

Further features of the present disclosure will become apparent from the following description of exemplary embodiments with reference to the attached drawings.

BRIEF DESCRIPTION OF THE DRAWINGS

FIG. 4 is a master table used for attribute setting in the first embodiment.

FIGS. 6A and 6B are diagrams illustrating exemplary displays of medical-treatment information according to the first embodiment.

FIG. 7 is a flowchart of a process performed by an information input support apparatus according to a second embodiment.

FIGS. 8A and 8B are diagrams illustrating exemplary displays of medical-treatment information according to the second embodiment.

FIG. 9 is a block diagram illustrating the functional configuration of an information input support apparatus according to a third embodiment.

FIGS. 10A and 10B are diagrams illustrating exemplary displays of medical-treatment information according to the third embodiment.

FIGS. 11A to 11D are diagrams illustrating exemplary displays of medical-treatment information according to a fifth embodiment.

DESCRIPTION OF THE EMBODIMENTS

An information input support apparatus will be described in detail below with reference to the drawings. Embodiments described below are examples, and these exemplary embodiments are not seen to be limiting.

First Embodiment

Functional Configuration of Information Input Support Apparatus

Figure 1:
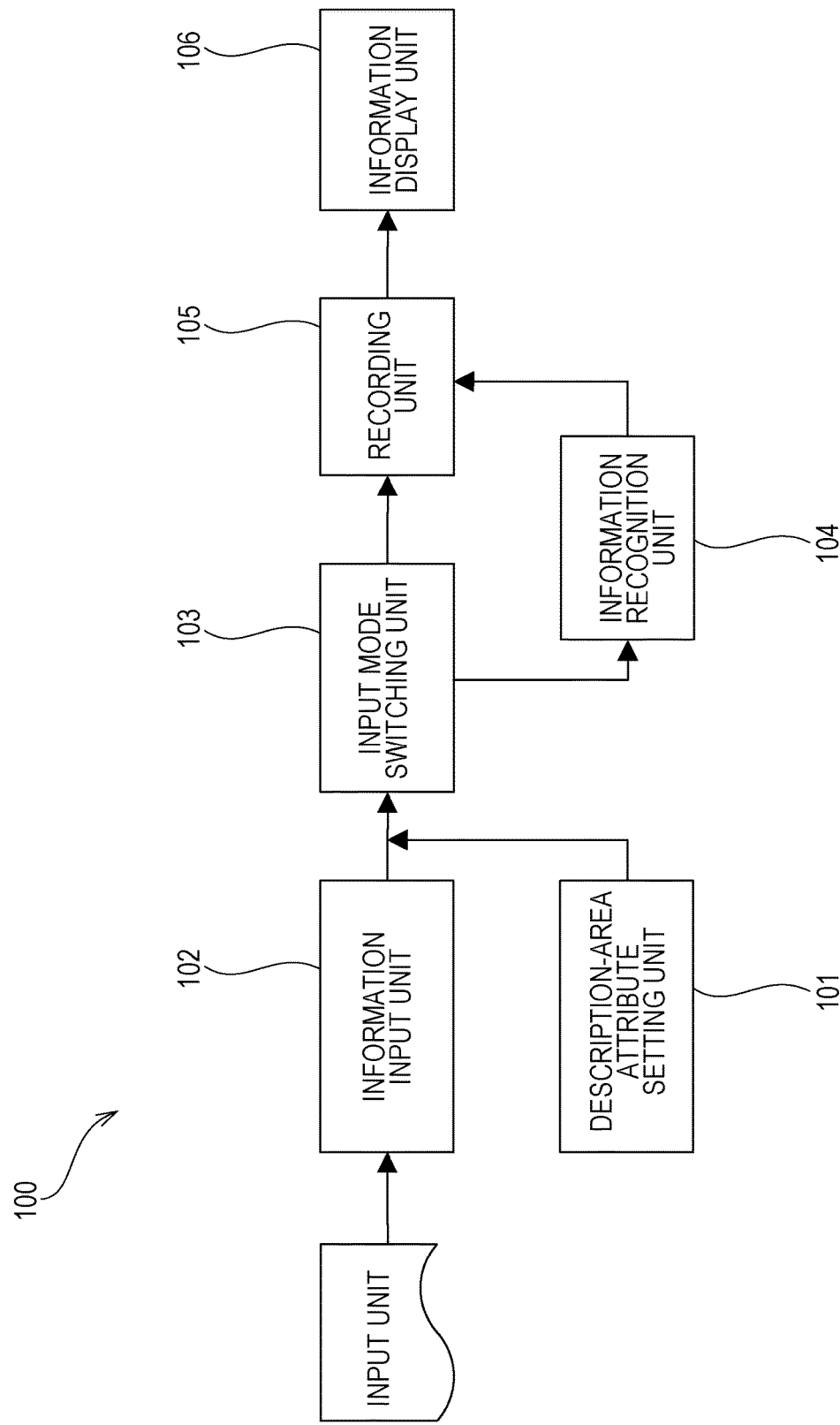
FIG. 1 is a block diagram illustrating the functional configuration of an information input support apparatus according to a first embodiment.

FIG. 1 is a block diagram illustrating an exemplary functional configuration of an information input support apparatus 100 according to a first embodiment. The information input support apparatus 100 functions as an information processing apparatus such as an information terminal which can be carried by a user.

The information input support apparatus 100 includes a description-area attribute setting unit 101, an information input unit 102, an input mode switching unit 103, an information recognition unit 104, a recording unit 105, and an information display unit 106. The description-area attribute setting unit 101 sets, in advance, pieces of attribute information of the S area, the O area, the A area, and the P area which are description areas obtained by dividing the display unit into multiple areas. The S (Subject) area is an area for writing the main complaints of a patient. The O (Object) area is an area for writing information obtained from medical tests. The A (Assessment) area is an area for writing a diagnosis made by a doctor. The P (Plan) area is an area for writing a treatment plan.

The information input unit 102 receives a description written on the display unit through an operation performed by a user using an input unit.

The input mode switching unit 103 switches the input mode between the handwriting input mode and the handwritten-input recognition mode in accordance with the attribute information of a description area.

The information recognition unit 104 recognizes handwritten description when the input mode is set to the handwritten-input recognition mode.

The recording unit 105 records a handwritten description, as it is, received by the information input unit 102 and the recognition result of a description which is recognized by the information recognition unit 104.

The information display unit 106 displays a handwritten description and the recognition result of a handwritten description which is recognized by the information recognition unit 104, on the display unit.

Figure 2:
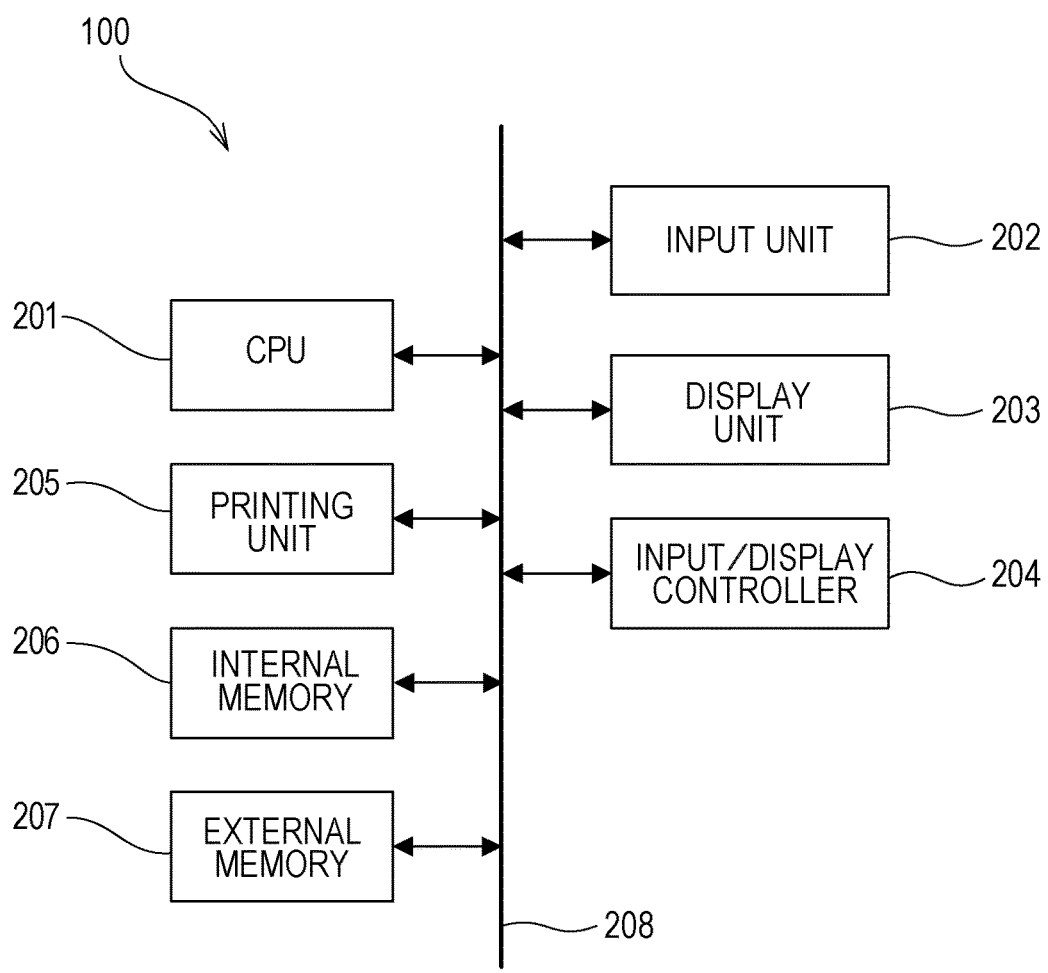
FIG. 2 is a block diagram illustrating the main configuration of the information input support apparatus according to the first embodiment.

FIG. 2 is a block diagram illustrating main components which enable the information input support apparatus 100 according to the first embodiment to be achieved. As illustrated in FIG. 2, the information input support apparatus 100 includes a central processing unit (CPU) 201, an input unit 202, a display unit 203, an input/display controller 204, a printing unit 205, an internal memory 206, and an external memory 207.

The CPU 201 is a central processing unit, and exerts overall control of the main components or the like of the information input support apparatus 100, which are described below. The CPU 201 executes programs stored in the internal memory 206 so as to achieve the functional configuration illustrated in FIG. 1 and the processes in flowcharts described below.

The input unit 202 is, for example, a pen-shaped pen-tablet pointer.

The display unit 203 is, for example, a liquid crystal display screen. A user operates the display unit 203 by using the input unit 202 or directly touches the display unit 203 so as to input characters and operational instructions. In the first embodiment, the description areas which are the S area, the O area, the A area and the P area are set in the display area of the display unit 203.

For example, a liquid crystal pen tablet in which the input unit 202 and the display unit 203 are integrated may be used as the input unit 202 and the display unit 203.

The input/display controller 204 controls the input unit 202 and the display unit 203 in accordance with the operating condition. For example, the input/display controller 204 switches the display of the input screen displayed on the display unit 203.

The printing unit 205 prints selected information.

The internal memory 206 functions as, for example, the main memory and a work area of the CPU 201, and stores programs executed by the CPU 201.

The external memory 207 is a storage of a personal computer (PC) and other media, such as a hard disk, a memory card, a compact flash (CF) card, a secure digital (SD) card, and a Universal Serial Bus (USB) memory.

Various types of data are transferred through a communication bus 208 between the components described above. For example, a signal for instructing the components that are to be controlled by the CPU 201 and data to be transmitted between the components are transferred to a predetermined processor.

The information input support apparatus 100 having the above-described configuration operates in accordance with various types of events transmitted from the input/display controller 204 or the like. When an interrupt is supplied from the input/display controller 204 or the like, an interrupt signal is transmitted to the CPU 201. This causes an event to occur, and the CPU 201 reads out various instructions stored in the internal memory 206 in accordance with the event, and executes various types of control.

The CPU 201 executes programs, thereby functioning as various units. A control circuit such as an application-specific integrated circuit (ASIC) which operates in coordination with the CPU 201 may function as these units. Alternatively, coordination between the CPU 201 and a control circuit may achieve these units. The CPU 201 is not necessarily a single CPU, and may be constituted by multiple CPUs. In this case, the multiple CPUs execute processes in a distributed manner. The multiple CPUs may be installed in a single computer, or may be installed in multiple computers which are physically different from each other. A dedicated circuit may achieve a unit implemented by the CPU 201 executing programs.

Operational Flow of Medical-Treatment Information Input Support

Figure 3:
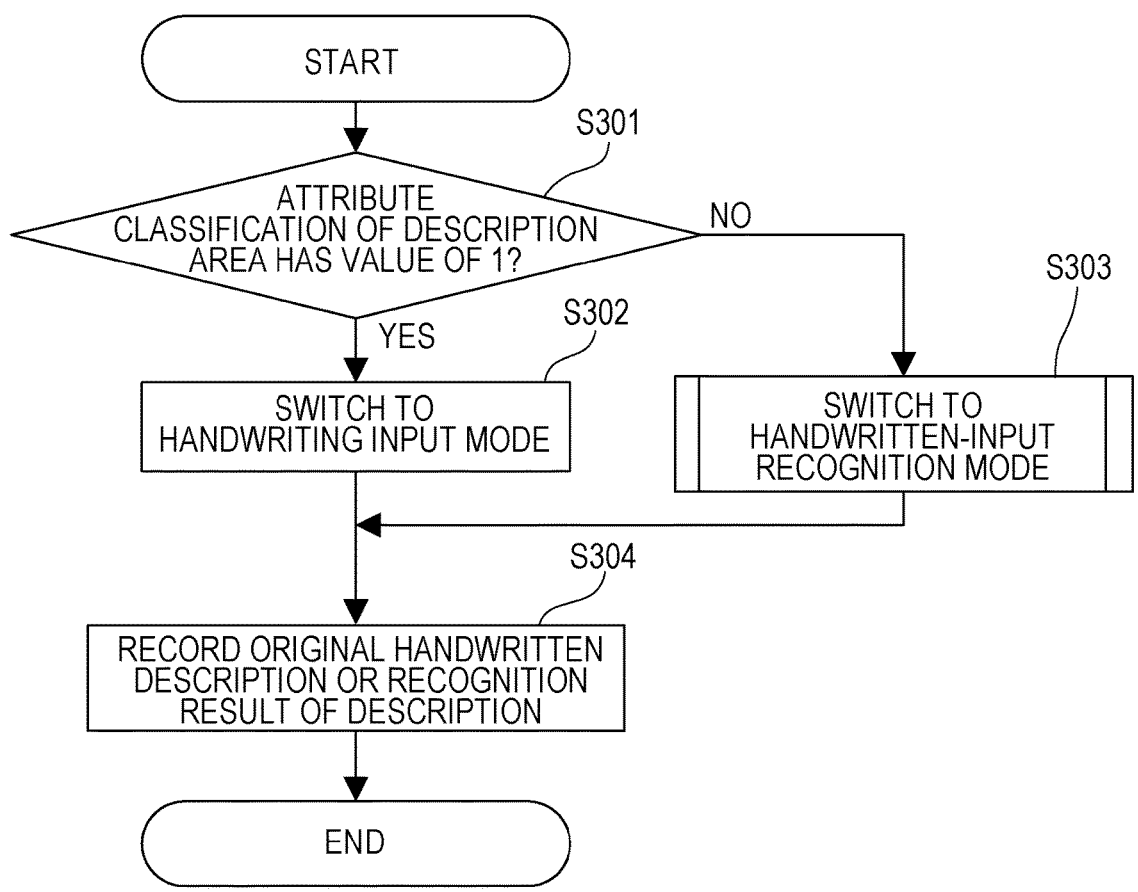
FIG. 3 is a flowchart of a process performed by the information input support apparatus according to the first embodiment.

FIG. 3 is a flowchart of a process of supporting input of medical-treatment information, which is performed by the information input support apparatus 100 according to the first embodiment. In the flowchart in FIG. 3, the process is started when a user writes medical-treatment information by using the input unit 202 on a description area which is set on the display unit 203.

In step S301, the information input unit 102 specifies a description area in which the user writes a description, among the description areas which are set by the display unit 203, and obtains attribute information which is set for the specified description area. The information input unit 102 determines whether or not the obtained attribute information is predetermined attribute information. Specifically, the information input unit 102 determines whether or not the attribute classification which is set for the description area has a value of 1. The attribute classification of a description area will be described below with reference to FIG. 4. If the attribute classification has a value of 1, the process proceeds to step S302. If the attribute classification does not have a value of 1, the process proceeds to step S303.

In step S302, the input mode switching unit 103 switches the input mode to the handwriting input mode. The handwriting input mode is a mode in which a handwritten description as it is (original description) is recorded or displayed. That is, in the handwriting input mode, medical data is recorded and displayed as image information as if a paper medical record is used.

In step S303, the input mode switching unit 103 switches the input mode to the handwritten-input recognition mode. The handwritten-input recognition mode is a mode in which a handwritten description is recognized and in which the recognition result is recorded and displayed. In the handwritten-input recognition mode, a handwritten description is converted into character information (electronic data), and the resulting character information is recorded and displayed. The process in the handwritten-input recognition mode will be described below with reference to FIG. 5.

In step S304, the recording unit 105 records the original handwritten description or the recognition result of the description on the basis of the attribute information of the input description area.

Specifically, if the attribute classification of the description area has a value of 1, the input mode is switched to the handwriting input mode. Accordingly, the recording unit 105 records the description in the description area as image information in the internal memory 206. The information display unit 106 displays the image information of the description in the description area of the display unit 203.

If the attribute classification of the description area has a value of 2, the input mode is switched to the handwritten-input recognition mode. Accordingly, the recording unit 105 records the character information obtained by converting the description in the description area, in the internal memory 206. The information display unit 106 displays the character information obtained by converting the description, in the description area of the display unit 203.

Even after the process in the flowchart in FIG. 3 is ended, the information display unit 106 displays the description recorded in the internal memory 206, in response to an operation of displaying the description, which is performed by a user. That is, if an original description is recorded, the information display unit 106 displays image information. If the recognition result of a description is recorded, the information display unit 106 displays character information on the display unit 203.

Attribute Setting for Description Area

Attribute setting for a description area will be described with reference to FIG. 4. FIG. 4 is a diagram illustrating a master table used for attribute setting for description areas. The master table contains an area ID, an area name, area bounds, and an attribute classification. The basic description areas in a medical record are the SOAP areas. For each of the SOAP areas, an area ID, area bounds for description, and an attribute classification number are set in such a manner as to be associated with each other. As the area bounds, pieces of coordinates information of the S area, the O area, the A area, and the P area which are obtained by dividing the display area of the display unit 203 into multiple areas are set. The attribute classification is set to 1 only for the S area referred to only by a doctor, whereas the attribute classification is set to 2 for the O area, the A area, and the P area which are shared by the other sections. The description-area attribute setting unit 101 sets the master table in advance, and stores the master table, for example, in the internal memory 206.

Therefore, in step S301, the information input unit 102 refers to the master table illustrated in FIG. 4, so as to obtain the attribute classification which is associated with and is set for the specified description area.

Handwritten Input Recognition in Step S303

Figure 5:
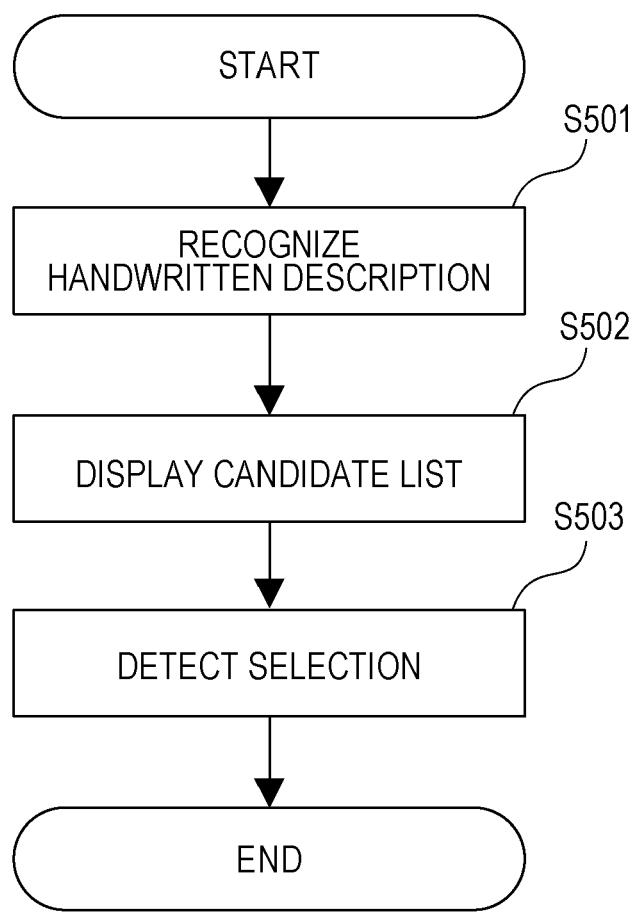
FIG. 5 is a flowchart of a process in a handwritten-input recognition mode in the first embodiment.

The detail of the process of recognizing a handwritten input, which is performed in the information input support according to the first embodiment will be described with reference to FIG. 5.

In step S501, the information recognition unit 104 recognizes the handwritten description. Specifically, the information recognition unit 104 recognizes handwritten characters and converts the characters to character information.

In step S502, the information recognition unit 104 generates a candidate list for the character information obtained through the conversion, on the basis of the recognition result. The information recognition unit 104 displays the generated candidate list on the display unit 203 in such a manner that a candidate can be selected from the candidate list.

In step S503, the information recognition unit 104 detects character information selected by the user from the candidate list. When the process returns back to the flowchart in FIG. 3, in step S304, the recording unit 105 records the character information detected by the information recognition unit 104.

Exemplary Medical-Treatment Information Input Support

FIGS. 6A and 6B are diagrams illustrating exemplary medical-treatment information displayed through the information input support according to the first embodiment. FIG. 6A is a diagram illustrating an exemplary description made when medical-treatment information is written. FIG. 6B is a diagram illustrating an exemplary result obtained through input support of the medical-treatment information in FIG. 6A.

In the S area, the O area, the A area, and the P area which are set on the display unit 203 illustrated in FIG. 6A, original handwritten descriptions are displayed.

After the input support, as illustrated in FIG. 6B, an original handwritten description is displayed in the S area on the display unit 203, and character information obtained through recognition of handwritten descriptions is displayed in the O area, the A area, and the P area.

Thus, according to the first embodiment, a user can check an original description or the recognition result of a description in accordance with the user's desire. In the first embodiment, medical-treatment information which is written by hand as if a paper medical record is used is switched between handwritten input data and handwritten input recognition data in accordance with the type of a description area. Therefore, while the advantages of paper medical records, i.e., usability and ease of evoking memories, are maintained, information sharing and unified management of electronic medical records can be achieved, improving quality and efficiency of medical service.

For example, in a description area which is often referred to by a doctor, the doctor can check an original description of medical-treatment information as if a familiar paper medical record is used, enhancing the ease of evoking memories of scenes of diagnosis. Therefore, while the operations and the convenience of traditional paper medical records are maintained, a doctor focuses his/her energy on a medical practice, improving quality of medical-treatment service. In contrast, in a description area in which information is to be shared among sections, handwritten medical-treatment information is converted into electronic formats, improving efficiency of medical service. In addition, in documents used in an industry other than the health industry, both of an original handwritten description and the recognition result of a description can be used by switching the input mode.

In the first embodiment described above, only the S area is set as a description area referred to only by a doctor, and the O area, the A area, and the P area are set as a description area to be shared. This exemplary embodiment is not limiting, and setting other than this may be employed.

In the first embodiment described above, the case is described in which the master table used for attribute setting for a description area contains an area ID, an area name, area bounds, and an attribute classification. Data other than these may be contained. Attribute values other than the attribute values which are set in the master table illustrated in FIG. 4 may be set.

In the first embodiment described above, the case is described in which a candidate list for character information is displayed in a description area in which input information is converted into the character information, while the information is being input. This exemplary embodiment is not seen to be limiting. For example, after information is written in all of the description areas, the recording unit 105 may switch between recording of an original handwritten description and recording of the recognition result of a description, in accordance with the attribute information of each of the description areas.

In the first embodiment described above, an original handwritten description is recorded in black characters, and the recognition result of a description is recorded as character information. Alternatively, determination as to whether or not characters in a handwritten description have a color other than black may be made. For example, when the recording unit 105 records the recognition result of a description as character information, the recording unit 105 determines whether or not characters in the description have a color, on the basis of the color information of character pixels. When the characters have a color, the recording unit 105 records character information with the color information, enabling the character color to be reproduced.

In the first embodiment described above, the case is described in which the description in a description area to be shared is recognized and in which the recognition result is recorded. This exemplary embodiment is not seen to be limiting. For example, the recording unit 105 may record coordinates information of a description on the display unit 203, with the recognition result of the description. Therefore, when the information display unit 106 displays the recognition result of a description, the information display unit 106 can display the recognition result in the same layout as that made when the information was written, on the display unit 203 on the basis of the recorded coordinates information. In addition, the recording unit 105 may record the character size of a description with the recognition result obtained through recognition. Therefore, when the information display unit 106 displays the recognition result of a description, the information display unit 106 may display the recognition result in the recorded character size on the display unit 203. In addition, the recording unit 105 may record the recognition result in such a manner that at least one of a predetermined format, a character size, and a character font is applied to the recognition result. The format, the character size, and the character font may be set in accordance with selection made by a user.

In the first embodiment described above, the case is described in which description areas are classified into two types, a description area that is to be shared and a description area that is not necessarily to be shared, and in which attribute information having a different value is set to each of the types. This exemplary embodiment is not seen to be limiting. For example, description areas may be classified into two types, a description area in which a handwritten description needs to be input and a description area in which input information may be converted into electronic formats, and attribute information having a different value may be set to each of these types.

Second Embodiment

In the first embodiment described above, under the assumption that a handwritten description contains only characters, the case is described in which switching is performed between the handwriting input mode and the handwritten-input recognition mode in accordance with the type of a description area. In a second embodiment, a case in which data other than a character, such as a schema image, is input will be described with reference to FIG. 7. In the second embodiment, the information input support apparatus 100 similar to that in the first embodiment may be used.

FIG. 7 is a flowchart of a process of information input support performed by the information input support apparatus 100 according to the second embodiment. In the flowchart in FIG. 7, the process is started when a user inputs medical-treatment information by using the input unit 202 in a description area which is set on the display unit 203.

In step S701, the information input unit 102 determines whether or not the attribute classification of the description area in which the user writes a description, among the description areas which are set on the display unit 203 has a value of 1. This process is similar to that in step S301 in FIG. 3 which is described above, and the description about the process will not made. If the attribute classification has a value of 1, the process proceeds to step S702. If the attribute classification does not have a value of 1, the process proceeds to step S703.

In step S703, the information input unit 102 determines whether or not the handwritten description forms characters. If the handwritten description forms characters, the process proceeds to step S704. If the handwritten description forms data other than a character, the process proceeds to step S702. Examples of data other than a character include a schema image. The determination as to whether or not the handwritten description forms characters may be made by the information input unit 102 detecting connected black pixels in the description and determining whether or not the pixels forms characters on the basis of the size of a rectangle containing the connected black pixels which are detected. For example, if the rectangle has a size less than a predetermined size, the information input unit 102 determines that the pixels form characters. If the rectangle has a size equal to or larger than the predetermined size, the information input unit 102 determines that the pixels form data other than a character.

In step S702, the input mode switching unit 103 switches the input mode to the handwriting input mode. Therefore, as described below, the original description in a description area whose attribute classification is set to 1, and, for example, a schema image in a description area whose attribute classification is set to 2 are recorded as image information, and are displayed on the display unit 203.

In step S704, the input mode switching unit 103 switches the input mode to the handwritten-input recognition mode. Therefore, the information recognition unit 104 recognizes the handwritten description. Accordingly, as described below, the recognition result of characters in a description area whose attribute classification is set to 2 is recorded, and is displayed on the display unit 203. This process may be performed similarly to that in the flowchart in FIG. 5.

In step S705, the recording unit 105 records the original handwritten description or the recognition result of the description on the basis of the attribute information of the input description area and the description.

Specifically, the recording unit 105 records the original description in a description area whose attribute classification is set to 1, and, for example, a schema image in a description area whose attribute classification is set to 2, as image information in the internal memory 206. The information display unit 106 displays image information of a description on the display unit 203.

In contrast, the recording unit 105 records character information obtained by converting a description in a description area whose attribute classification is set to 2, in the internal memory 206. The information display unit 106 displays the character information of the description on the display unit 203.

Similarly to the first embodiment, in the second embodiment, in the master table, only the attribute classification of the S area which is a description area referred to only by a doctor is set to 1, and the attribute classifications of the O area, the A area, and the P area which are shared among the other sections are set to 2.

Exemplary Medical-Treatment Information Input Support

FIGS. 8A and 8B are diagrams illustrating exemplary medical-treatment information displayed through the information input support according to the second embodiment. FIG. 8A is a diagram illustrating an exemplary description made when medical-treatment information is written. FIG. 8B is a diagram illustrating an exemplary result obtained by supporting input of the medical-treatment information in FIG. 8A.

A schema image is written in the outside of the S area on the display unit 203 illustrated in FIG. 8A.

As illustrated in FIG. 8B, after the input support, the description in the S area and the schema image on the display unit 203 are displayed as they are, and pieces of character information obtained by converting the handwritten descriptions are displayed in the O area, the A area, and the P area.

Thus, according to the second embodiment, when, for example, a schema image which is data other than a character is written, the original image data which is written can be recorded and displayed as it is.

Third Embodiment

In the first and second embodiments described above, the case is described in which an attribute classification is set for a description area and in which switching is performed between the handwriting input mode and the handwritten-input recognition mode in accordance with the attribute classification of a description area. In a third embodiment, both of a handwritten description and the recognition result of the handwritten description are recorded, and display of the description is switched when necessary.

Functional Configuration of Information Input Support Apparatus

FIG. 9 is a block diagram illustrating the functional configuration of an information input support apparatus 900 according to the third embodiment.

The information input support apparatus 900 includes an information input unit 901, an input-data recording unit 902, an information recognition unit 903, a recognition-result recording unit 904, and an information display switching unit 905.

The information input unit 901 receives a description which is written on the display unit 203 in accordance with operations performed by a user by using the input unit 202.

The input-data recording unit 902 records the original handwritten description which is received by the information input unit 901. Specifically, the input-data recording unit 902 records the handwritten description as image information in the internal memory 206.

The information recognition unit 903 recognizes the handwritten description from the information input unit 901. Specifically, the information recognition unit 903 converts the handwritten description into character information.

The recognition-result recording unit 904 records the recognition result obtained by the information recognition unit 903 recognizing a handwritten description. Specifically, the recognition-result recording unit 904 records character information obtained through conversion of a handwritten description, in the internal memory 206.

The information display switching unit 905 switches between the data recorded by the input-data recording unit 902 and the data recorded by the recognition-result recording unit 904 in accordance with selection made by a user, so as to display the selected data on the display unit 203.

In the third embodiment, for one description, the input-data recording unit 902 records the original description, and the recognition-result recording unit 904 records character information obtained through conversion of the description.

The main components which allow the information input support apparatus 900 to be achieved have a configuration similar to that in the block diagram in FIG. 2.

Exemplary Medical-Treatment Information Input Support

FIGS. 10A and 10B are diagrams illustrating exemplary medical-treatment information displayed through the information input support according to the third embodiment. FIG. 10A is a diagram illustrating an exemplary display of the original description of medical-treatment information. FIG. 10B is a diagram illustrating an exemplary display of the recognition result of the handwritten description in FIG. 10A. FIG. 10A illustrates a display for a doctor making diagnosis, and FIG. 10B illustrates a display for medical practices and medical office work.

Thus, in the third embodiment, a user can check an original description or the recognition result of a description in accordance with the user's desire. That is, both of an original handwritten description and the recognition result of a handwritten description are recorded, enabling display of the description to be switched in accordance with user's convenience.

In the third embodiment described above, the case is described in which switching is performed between display of an original handwritten description and display of the recognition result of a handwritten description in all of the description areas. This exemplary embodiment is not seen to be limiting. For example, as illustrated in the master table in FIG. 4, attribute information may be set to each of the description areas, and the information display switching unit 905 may switch between display of an original handwritten description and display of the recognition result of a handwritten description in accordance with the attribute information of a description area.

Fourth Embodiment

In the first and second embodiments, the case is described in which, using a medical record written in the S area, the O area, the A area, and the P area, the input mode is switched in accordance with the type of a description area. In the third embodiment, the case is described in which, for a description in a medical record, switching is performed between display of an original handwritten description and display of the recognition result of a handwritten description. In a fourth embodiment, a case in which a medical document other than a medical record is used will be described.

In hospitals, other than a medical record, various types of medical documents, such as a consent form, a medical test data sheet, and a recording list, are used. These medical documents have a description area in which an original handwritten description needs to be recorded and a description area in which an original handwritten description does not need to be recorded. Examples of a description area in which an original handwritten description needs to be recorded include a sign field (sign area) for checking identification of a person filling out the form. Therefore, the description-area attribute setting unit 101 sets areas in which a handwriting input is necessary, in advance for these medical documents. The input mode switching unit 103 may switch the input mode between the handwriting input mode and the handwritten-input recognition mode in accordance with registration of the areas. Specifically, the description-area attribute setting unit 101 sets the attribute classification to 1 for a sign area in accordance with an operation performed by a user using the input unit 202. Therefore, the input mode switching unit 103 switches the input mode to the handwriting input mode when the sign area is filled in. Another way of setting an area may be used.

Fifth Embodiment

In the first to fourth embodiments, the case is described in which, under the assumption that a pen-tablet pointer is used as an input medium, the input mode is switched in accordance with the type of a description area on the basis of an online character recognition technique.

Basically, techniques of recognizing a handwritten description and converting it into character information are roughly classified into offline character recognition and online character recognition. In online character recognition, candidates of character information are determined on the basis of the stroke order and the trace of a character which is input. In offline character recognition, candidates of character information are determined from the image data of a handwritten character. In the fifth embodiment, a case will be described in which a paper medical document is used as an input medium and in which the input mode is switched in accordance with the type of a description area on the basis of an offline character recognition technique.

In hospitals, various types of paper medical documents, such as a paper medical record, a medical interview sheet, or a consent form, are scanned to be converted into electronic forms. For these paper medical documents, the input mode is switched in accordance with the type of a description area on the basis of the offline character recognition technique. Specifically, the description-area attribute setting unit 101 specifies the coordinates of an area in which a handwritten description is to remain as it is, and the coordinates of an area in which a description is to be converted into electronic formats, on a paper medium in advance, and sets such coordinates. For example, when each of entry fields filled in by a doctor or the like in the paper medical record is associated with a category, such as "S", "O", "A", or "P", in advance, it is possible to define the coordinates of an area in which a handwritten description is to remain as it is, and to define the coordinates of an area in which a description is to be converted into electronic formats, in advance as described above. The input mode switching unit 103 causes a description in a description area which is set as an area in which a handwritten description is to remain as it is, to be output as a handwritten description, and causes a description in a description area which is set as an area in which a description is to be converted into electronic formats, to be recognized by using the offline recognition technique.

Another way of setting an area is as follows. For example, a document processing technique is used to obtain a block of each of character areas. If the recognition result of the block of a character area includes a specified string, the character area is set as an area in which a description is to be converted into electronic formats. If the recognition result of the block of a character area does not include the specified string, the character area is set as an area in which a handwritten description is to remain as it is. This way of setting an area will be described with reference to FIGS. 11A to 11D.

FIGS. 11A to 11D illustrate exemplary medical-treatment information displayed through the information input support according to the fifth embodiment. FIG. 11A is a diagram illustrating an exemplary display of a handwritten description of medical-treatment information in a paper medical record. FIG. 11B is a diagram illustrating an exemplary display of the recognition result of the handwritten description in FIG. 11A, and a rectangular frame indicates the block of a character area obtained through the document processing. FIG. 11C illustrates an exemplary specification of strings included in target areas whose attribute classification has a value of 1, that is, in which a description is to be converted into electronic formats. FIG. 11D illustrates an exemplary result obtained by switching the handwriting mode in accordance with the type of a description area. Specifically, if the recognition result in FIG. 11B contains a string specified in FIG. 11C, the character area is set as an area in which a description is to be converted into electronic formats, and the recognition result of the character area is output. In contrast, in an area which does not contain a string specified in FIG. 11C, a handwritten description is displayed. In the example illustrated in FIG. 11C, in an area containing "0", "findings", and "test", instead of a handwritten description, characters in electronic forms which are obtained through character recognition are displayed. Alternatively, in an area containing at least one of "0", "findings", and "test", instead of a handwritten description, characters in electronic forms which are obtained through character recognition may be displayed. A block in a document, for which whether or not "0", "findings", "test", and the like are contained is checked, is determined, for example, on the basis of the space between characters or between symbols.

Unlike the example in FIG. 11C, the table may have information directly representing an area in which a handwritten description is to be displayed as it is. For example, an area which contains a character such as "S" may be set as an area in which a handwritten description is to be displayed as it is. An area which does not contain a character such as "S" may be set as an area for which character recognition is performed so that characters in electronic formats are displayed.

If the recognition result of a character area in FIG. 11B does not contain a string specified in FIG. 11C, the character area is set as a handwritten description area, and a handwritten description is displayed as it is.

The way of setting an area in which a handwritten description is to remain as it is and an area in which a description is to be converted into electronic formats is not limited to the example described above. Another way of setting an area may be used.

Sixth Embodiment

In the first to fifth embodiments, a case is described in which a medical document specializing in medical care is processed. In a sixth embodiment, a case in which a document used in a field other than medical care is processed will be described.

In industries other than medical care, for example, in a bank or a real-estate agent, many documents, such as a deposit form and a contract document, are used. In these documents, conversion of data, for example, in a sign field into character information makes it impossible to check authenticity of the document. Therefore, a record of an original handwritten description and a record of the recognition result of a handwritten description may be differentiated from each other. These documents have a determined format. Accordingly, an area for which a handwritten description needs to be recorded, such as a sign field, is registered. Switching is performed between the handwriting input mode and the handwritten-input recognition mode in accordance with the registration information of a description area, achieving both of authenticity and sharing of information.

Other Embodiments

Additional embodiments can also be realized by a computer of a system or apparatus that reads out and executes computer executable instructions recorded on a storage medium (e.g., computer-readable storage medium) to perform the functions of one or more of the above-described embodiment(s), and by a method performed by the computer of the system or apparatus by, for example, reading out and executing the computer executable instructions from the storage medium to perform the functions of one or more of the above-described embodiment(s). The computer may comprise one or more of a (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2013-159741 filed Jul. 31, 2013, which is hereby incorporated by reference herein in its entirety.

What is claimed is:

1. An information processing apparatus comprising:
a processor and a memory coupled to the processor, the memory having instructions stored thereon that are executed by the processor to act as:
a receiving unit configured to receive a handwritten input for a description area displayed on a display unit;
an information recognition unit configured to recognize a description of the handwritten input written in the description area and to convert the description to character information;
an acquiring unit configured to acquire positional information of the description area in which the handwritten input is received;
a determining unit configured to determine whether to display image information of the description written in the description area or to display the character information of the description written in the description area based on the positional information acquired by the acquiring unit; and
a display control unit configured to cause the display unit to display the image information of the description written in the description area or the character information of the description written in the description area in accordance with a determination result obtained by the determining unit,
wherein, in a case where the description includes data other than one or more characters written in the description area in which the character information of the description is displayed, the display control unit causes the display unit to display the data other than the one or more characters.

2. The information processing apparatus according to claim 1,
wherein the display unit displays a selectable candidate list of the character information obtained by the information recognition unit converting the description when the positional information acquired by the acquiring unit indicates that the display unit displays the character information.

3. The information processing apparatus according to claim 1, further comprising the executed instructions to act as:
a setting unit configured to set positional information of an area in which is displayed as the image information and positional information of an area in which is displayed as the character information.

4. The information processing apparatus according to claim 1,
wherein the description area is an area in which a description is written, and the description includes at least one of a main complaint, a test, a diagnosis, and a treatment plan.

5. The information processing apparatus according to claim 1, wherein the acquiring unit acquires positional information of an area in which a main complaint is described as the positional information of the description area in which the description is written, and wherein the positional information of the area in which the main complaint is described indicates that the display unit displays the image information.

6. The information processing apparatus according to claim 1, wherein the description is acquired by scanning a paper document.

7. The information processing apparatus according to claim 1, wherein the information recognition unit is configured to recognize the description of the handwritten input written in the description area and to convert the description to the character information, in a case where the determining unit determines to display the character information of the description written in the description area.

8. The information processing apparatus according to claim 7, wherein the information recognition unit is configured not to recognize the description of the handwritten input written in the description area and not to convert the description to the character information, in a case where the determining unit determines to display the image information of the description written in the description area.

9. A method for controlling an information processing apparatus, the method comprising:
 receiving a handwritten input for a description area displayed on a display unit;
 recognizing a description of the handwritten input written in the description area and converting the description to character information;
 acquiring positional information of the description area in which the handwritten input is received;
 determining whether to display image information of the description written in the description area or to display the character information of the description written in the description area based on the acquired positional information; and
 causing the display unit to display the image information of the description written in the description area or the character information of the description written in the description area in accordance with a determination result obtained in the determining,
 wherein, in a case where the description includes data other than one or more characters written in the description area in which the character information of the description is displayed, the causing includes causing the display unit to display the data other than the one or more characters.

10. A non-transitory computer-readable storage medium storing computer executable instructions that cause a computer to execute a method comprising:
 receiving a handwritten input for a description area displayed on a display unit;
 recognizing a description of the handwritten input written in the description area and converting the description to character information;
 acquiring positional information of the description area in which the handwritten input is received;
 determining whether to display image information of the description written in the description area or to display the character information of the description written in the description area based on the acquired positional information; and
 causing the display unit to display the image information of the description written in the description area or the character information of the description written in the description area in accordance with a determination result obtained in the determining,
 wherein, in a case where the description includes data other than one or more characters written in the description area in which the character information of the description is displayed, the causing includes causing the display unit to display the data other than the one or more characters.

* * * * *